United States Patent [19]
Onodera et al.

[11] Patent Number: 5,542,939
[45] Date of Patent: Aug. 6, 1996

[54] FLUID ASPIRATION-COLLECTION APPARATUS

[75] Inventors: Hisashi Onodera, Kyoto; Junichi Yamanaka, Osaka, both of Japan

[73] Assignee: Daiken Iki Co., Ltd., Japan

[21] Appl. No.: 327,403

[22] Filed: Oct. 21, 1994

[30] Foreign Application Priority Data

Oct. 26, 1993 [JP] Japan .................................. 5-267445

[51] Int. Cl.⁶ .................................................. A61M 1/00
[52] U.S. Cl. .............................. 604/319; 92/59; 604/317; 417/469
[58] Field of Search ..................... 604/118, 119, 604/121, 317, 319, 321; 417/469, 472; 92/57, 146

[56] References Cited

U.S. PATENT DOCUMENTS

| | | |
|---|---|---|
| 4,112,949 | 9/1978 | Rosenthal et al. . |
| 4,397,643 | 8/1983 | Rygiel .................................. 604/317 |
| 4,429,693 | 2/1984 | Blake et al. ........................... 604/73 |
| 4,578,060 | 3/1986 | Huck et al. . |
| 5,073,172 | 12/1991 | Fell ....................................... 604/119 |
| 5,102,404 | 4/1992 | Goldberg et al. ...................... 604/317 |
| 5,185,007 | 2/1993 | Middaugh et al. .................... 604/320 |

FOREIGN PATENT DOCUMENTS 3326250  1/1985  Germany ............................ 417/472
2261472  3/1989  Japan .

*Primary Examiner*—Mary Beth Jones
*Assistant Examiner*—Mark O. Polutta
*Attorney, Agent, or Firm*—Sixbey, Friedman, Leedom & Ferguson, P.C.; David S. Safran

[57] ABSTRACT

The present invention pertains to a fluid aspiration-collection apparatus for aspirating and collecting a fluid into a suction chamber through a fluid inlet communicating with the suction chamber in the case, and for discharging the fluid through a fluid outlet after completion of fluid aspiration. A primary object of the present invention is to provide an apparatus which is simple in construction and is capable of aspirating the fluid at a constant pressure. The apparatus of the present invention comprises a case having a suction chamber formed, interior of which communicates with a fluid inlet and a fluid outlet, a moving plate constituting a part of a wall section of the suction chamber and movably disposed within the case; and a cylinder in which a piston is airtightly and movably inserted and in which a vacuum chamber is created by relative movement of the piston or itself; the piston and the moving plate being connected to move together; the cross sectional area of the piston being set smaller than the projected area in the direction of movement of the moving plate; and the back side of the piston and the moving plate communicating with the atmosphere.

19 Claims, 9 Drawing Sheets

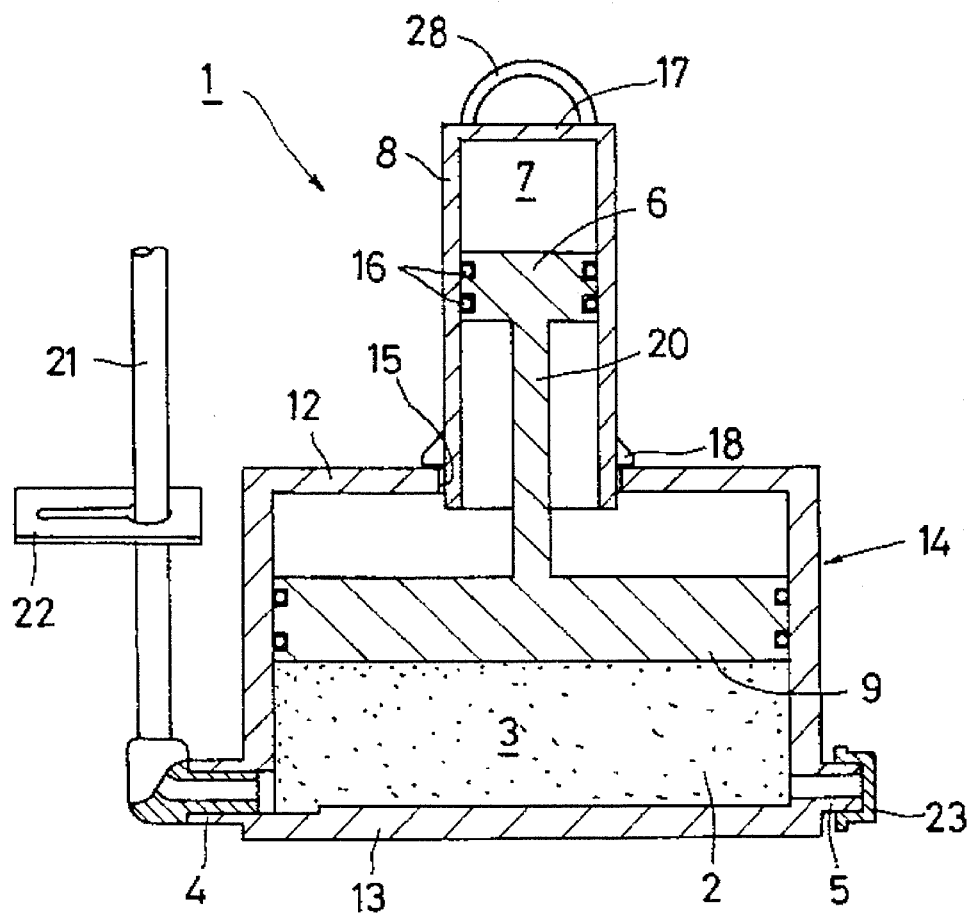
FIG. 2
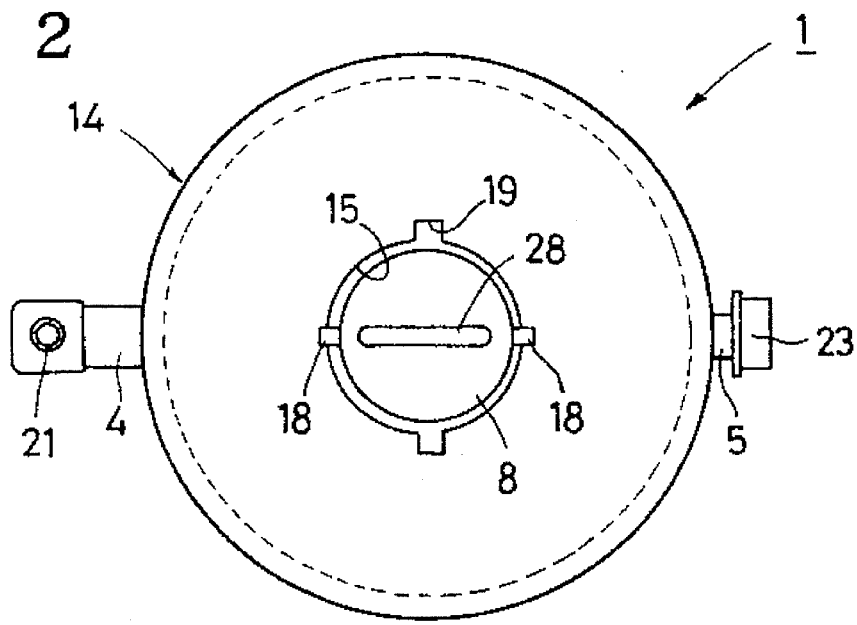

FLUID ASPIRATION-COLLECTION APPARATUS

FIELD OF THE INVENTION AND RELATED STATEMENT

The present invention relates to a fluid aspiration-collection apparatus for aspirating and collecting a fluid including a body fluid such as blood and lymph generated during medical treatment or surgery for injury and disease, blood and secreting fluid generated in a cavity after surgery, a physiological saline solution after flushing an operated part or an oral cavity, and a waste liquid including urine and stool.

An aspiration-collection apparatus comprising an elastic, expansible bellows-type container is known in the prior art as disclosed in Unexamined Japanese Patent Publication No. Hei 2-261472. A method of using the container includes pre-compressing the container before use to extrude the air inside, building up a negative pressure within a suction chamber in the container by utilizing an elastic restoring force of the container, sucking the liquid at a fluid inlet communicating with the suction chamber, and, after the collection of the fluid, compressing the container again to discharge the fluid filled in the suction chamber out at a fluid outlet.

In the bellows-type aspiration-collection apparatus, because the elastic restoring force of the bellows-type container increases on the contraction stroke and decreases on the expansion stroke, a relatively big negative pressure is created in the suction chamber during the initial period of aspiration; however, as the container sucks the fluid and expands, the suction pressure gradually decreases. That is, the aspiration-collection apparatus has the disadvantage that fluid aspiration can not be done at a constant suction pressure.

There will occur various problems if the suction pressure varies. For example, when the aspiration-collection apparatus is used in medical treatment or surgery, exudation of blood and secreting fluid from an affected part will be accelerated under a high suction pressure. Also there will arise such a disadvantage that the tissue of internal organs will be sucked to the opening of an aspiration tube which is connected to a fluid inlet, resulting in tissue trauma. In the meantime, if the suction pressure is too low, it will be difficult to aspirate the fluid from the region where suction tube is inserted, resulting in delayed recovery of the affected part. Therefore, this type of fluid aspiration-collection apparatus requires a constant suction pressure.

An apparatus having an inflatable-expansible balloon member in a rigid container is used as an apparatus capable of producing as much a constant suction pressure as possible, as disclosed in Examined Japanese Patent Publication No. Sho 63-1859. This apparatus is of such a design that the balloon member is inflated before use to extrude the air inside the rigid container, and then the balloon member is allowed to contract to build up the negative pressure, by utilizing the shrinkage force of the balloon member, within the suction chamber in the rigid container.

OBJECT AND SUMMARY OF THE INVENTION

The above-mentioned apparatus, however, has such a disadvantage that when the balloon member is inflated, the surface of the member touches the inner surface of the rigid container, and when the balloon inflation is restrained, the shrinkage force of the balloon member varies as aspiration goes on, failing in producing a constant negative pressure. Furthermore the apparatus is complicated in construction and large in size, consequently becoming costly.

In view of the above-described various disadvantages inherent in the heretofore known arts, it is an object of the present invention to provide a fluid aspiration-collection apparatus which can always produce a constant suction pressure regardless of the volume of fluid aspirated.

The fluid aspiration-collection apparatus of the present invention comprises a case having a suction chamber interior which communicates with a fluid inlet and a fluid outlet, a moving plate constituting a part of the wall section of the suction chamber and movably disposed within the case, and a cylinder in which a piston is airtightly and movably inserted and in which a vacuum chamber is created by the relative movement of the piston itself, the piston and the moving plate being connected to move together, the cross sectional area of the piston being set smaller than the projected area in the direction of movement of said moving plate, and the back side of the piston and the moving plate communicating with the atmosphere.

When the cylinder is movable with respect to the case (see FIGS. 1 to 8), the moving plate is moved to reduce the volume of the suction chamber to a minimum. The piston is held in contact with the closed end of the cylinder and with either one of the fluid inlet or the fluid outlet communicating with the suction chamber in communication with the atmosphere and with the suction chamber kept communicating with the atmosphere. In this case, since the moving plate and the piston are connected to move together, the piston and the cylinder also move with the movement of the moving plate. Subsequently, when the cylinder is moved while the fluid inlet and the fluid outlet are closed, the vacuum chamber is created within the cylinder. When the vacuum chamber is created, the back side of the piston and the moving plate are exposed to the atmosphere; and because the sectional area of the piston is set smaller than the projected area in the direction of movement of the moving plate, the moving plate and the piston are held in a stationary state (see FIG. 4).

On the other hand, when the cylinder is fixedly mounted on the case (see FIGS. 9 and 10), and the moving plate is moved to reduce the volume of the suction chamber as small as possible with the piston held in contact with the closed end of the cylinder and with the suction chamber communicating with the atmosphere, the piston connected with the moving plate also moves in the cylinder with the movement of the moving plate, thus forming the vacuum chamber within the cylinder. When, after the reduction of the suction chamber volume to a minimum, the fluid inlet and the fluid outlet are closed from the atmosphere, this state will be maintained because the back side of the piston and the moving plate are exposed to the atmosphere and the sectional area of the piston has been set smaller than the protected area in the direction of movement of the moving plate.

When the fluid inlet is open to the fluid to be aspirated, the fluid is drawn into the suction chamber and at the same time the moving plate moves towards increasing the volume of the suction chamber according to the amount of fluid to be aspirated. At this time, the negative pressure to be built up in the suction chamber is determined merely by the ratio of the sectional area of the piston to the projected area in the direction of movement of the moving plate, and the atmosphere, regardless of the quantity of fluid to be aspirated, and accordingly there is always produced a constant negative pressure in the suction chamber.

To discharge the fluid collected in the suction chamber, the fluid inlet is closed and at the same time the fluid outlet is opened and then the moving plate is moved towards decreasing the volume of the suction chamber. In this case, the cylinder is moved towards the piston side or the air is led into the vacuum chamber, so that the negative pressure for pulling up the moving plate will be removed to permit easy discharge of the fluid.

According to the present invention, therefore, the apparatus of simple construction can constantly produce a fixed negative pressure within the suction chamber.

BRIEF DESCRIPTION OF THE DRAWINGS

In the accompanying drawings:

FIG. 1 is a sectional view of a first embodiment of a fluid aspiration-collection apparatus according to the present invention;

FIG. 2 is a plan view of FIG. 1;

DETAILED DESCRIPTION OF THE PREFERRED EMBODIMENTS

First Embodiment

Figure 3:
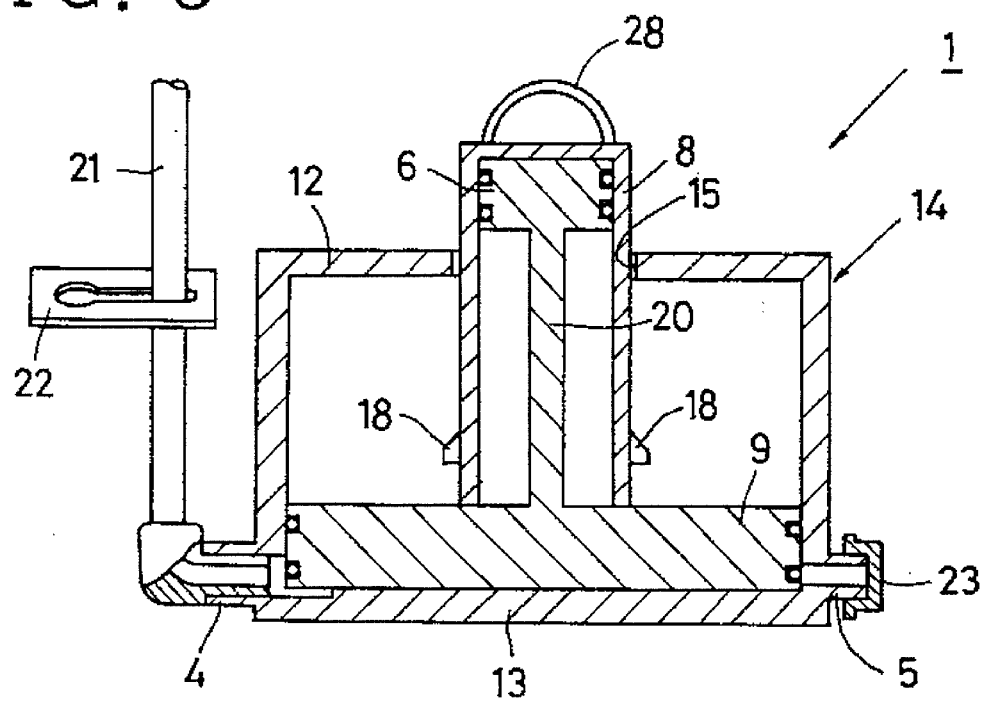
FIG. 3 is an explanatory view of operation of the same embodiment of the fluid aspiration-collection apparatus.

A fluid aspiration-collection apparatus 1 pertaining to a first embodiment shown in FIGS. 1 to 4 comprises a sturdy, cylindrical case 14 having an upper wall 12 and a lower wall 13. The case 14 is formed of a transparent or semitransparent thermoplastic synthetic resin. For the synthetic resin there may be used an easily moldable rigid synthetic resin such as polyvinyl chloride, polypropylene, polyethylene, polycarbonate, etc. It should be noted that the case 14 is not limited in shape to the cylindrical type and may be for example a square-tube type.

A round hole 15 is provided in the central part of the upper wall 12 of the case 14. In this round hole 15 is vertically and movably inserted a cylindrical cylinder 8 which is open at bottom. In this cylinder 8 a piston 6 is airtightly and vertically movably provided; the back side (the lower surface in the present embodiment) of the piston 6 communicates with the atmosphere. The piston 6 is provided with a seal ring 16 on the outer periphery so that it may slide airtightly in relation to the cylinder 8. When the piston 6 is moved relative to the cylinder 8 from the position in which the piston 6 is in contact with the upper wall 17 constituting the closed end of the cylinder 8, a vacuum chamber 7 is formed within the cylinder 8.

To hold the piston 6 in contact with the upper wall 17 of the cylinder 8, a communicating port (not illustrated) communicating with both the vacuum chamber 7 and the atmosphere is provided in the upper wall 17 of the cylinder 8, and after the piston 6 is slid upwardly until it contacts the upper wall 17 of the cylinder 8, the communication port is closed airtightly by a closing means such as a plug. This closing means may be fixedly attached by either bonding or welding at the time of closing.

On the cylinder 8 is provided a handle 28. The cylinder 8 and the piston 6 are formed of a rigid synthetic resin. On the outer periphery of the lower end of the cylinder 8 is provided a locking projection 18 constituting a holding means for holding the position of the cylinder 8 relative to the case 14. The locking projection 18 engages the cylinder from above with the upper wall 12 of the case 14 when the cylinder 8 is pulled upwardly relative to the case 14, thus preventing the downward movement of the cylinder 8. A part of the round hole 15 of the case 14 is radially outwardly cut out as shown in FIG. 2, so that the locking projection 18 can pass through a cutout 19. The downward movement of the cylinder 8 is checked by rotating the cylinder 8 after the passing of the locking projection 18 through the cutout 19.

In the case 14 a disk-like moving plate 9 is vertically and movably installed. The moving plate 9 is fitted with seal rings on the outer periphery, so that the moving plate will slide airtightly relative to the case 14. Under the moving plate 9 is formed the suction chamber 3. That is, the moving plate 9 forms a part of the wall of the suction chamber 3, and is so designed that the volume of the suction chamber 3 increases and decreases with the vertical movement of the moving plate. The projected area $S_9$ in the direction of movement of the moving plate 9 is set larger than the sectional area $S_6$ of the piston 6, and the back side (the upper surface in the present embodiment) of the moving plate 9 communicates with the atmosphere through a gap between the cylinder 8 and the round hole 15 of the upper wall 12 of the case 14. In the present embodiment, the moving plate 9 is a plate-like member and moves in the normal direction with respect to the bottom surface of the moving plate, and therefore the projected area $S_9$ in the direction of movement of the moving plate 9 is equal to the sectional area of the moving plate 9 or the area of the bottom surface.

The moving plate 9 and the piston 6 are connected as one unit by a connecting rod 20 so that they will move together. The moving plate 9, the piston 6 and the connecting rod 20 may be formed integrally, or may be fixed into one unit after being separately molded. Therefore, with the upward movement of the piston, the moving plate 9 also moves upwardly, thus increasing the volume of the suction chamber 3.

A fluid inlet 4 and a fluid outlet 5 which communicate with the interior of the suction chamber 3 are provided at the lower end of the side wall of the case 14. To the fluid inlet is connected a flexible fluid guide tube 21. The fluid inlet 4 can be opened and closed by sliding a plate clamp 22 mounted on the fluid guide tube 21. On the fluid outlet a cap 23 is removably, airtightly, and fluid-tightly fitted. The fluid outlet 5 can be opened and closed by installing and removing the cap 23. Also the suction chamber 3 can be closed by closing the fluid inlet 4 and the fluid outlet 5. Valve devices may be used as means for opening and closing the fluid inlet 4 and the fluid outlet 5.

Figure 4:
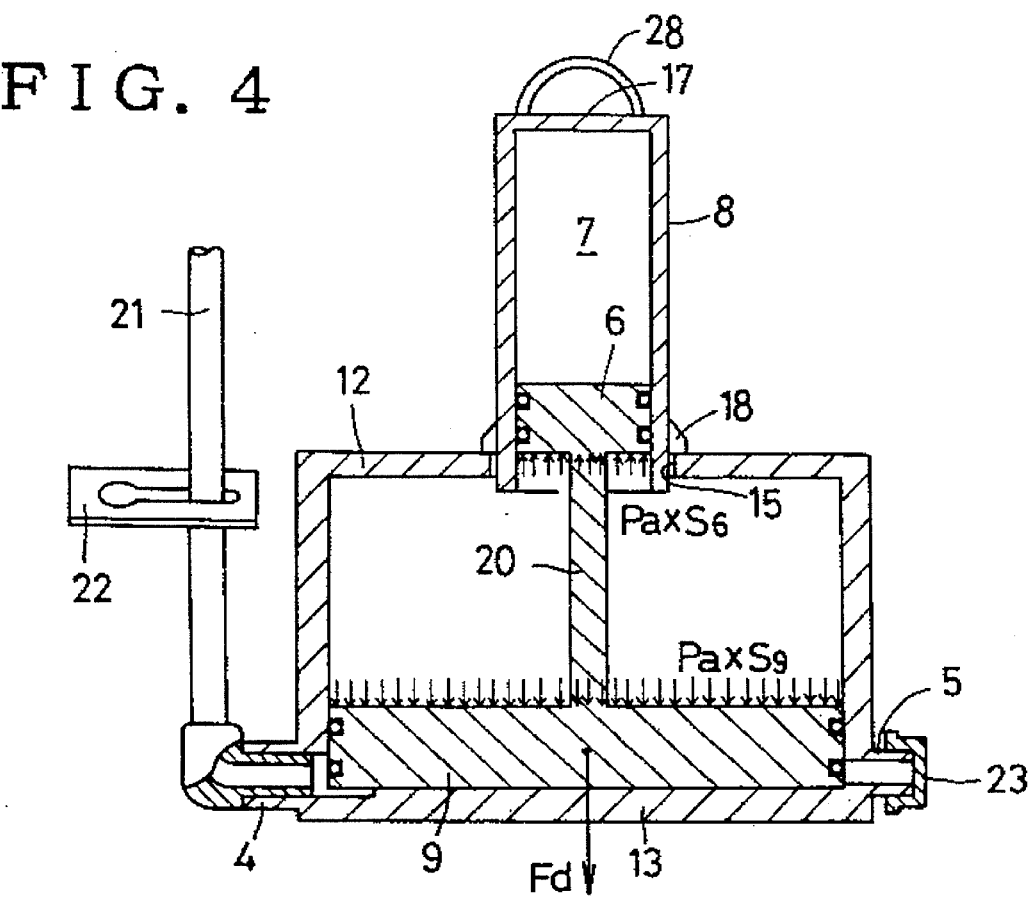
FIG. 4 is an explanatory view of operation of the same embodiment of the fluid aspiration-collection apparatus.

When the fluid aspiration-collection apparatus 1 of the present embodiment is used, first the moving plate 9 is pushed downwardly until it contacts the lower wall 13 of the case 14 as shown in FIG. 3. Then the suction chamber 3 is closed by closing the fluid inlet 4 and the fluid outlet 5. In this state, the cylinder 8 is pulled upwardly to form the vacuum chamber 7 as shown in FIG. 4, and the locking projection 18 of the cylinder 8 is set from above on the upper wall 12 of the case 14, thereby restraining the downward movement of the cylinder relative to the case 14. At this time, a downward force by the atmospheric pressure is applied to the cylinder 8 in an attempt to decrease the volume of the vacuum chamber 7, but the cylinder 8, being locked by the locking projection 18 as stated above, is restrained from moving downwardly.

When the suction chamber 3 is in a closed state, the piston 6 and the moving plate 9 which are connected in a unit, and subjected to the downward force Fd by the atmospheric pressure, remain stationary without moving upwardly. That is, let Pa be the atmospheric pressure, $S_6$ be the sectional area of the piston 6, and $S_9$ be the projected area in the direction of movement of the moving plate, and the force Fd will be obtained by the formula (1) given below. It is clear from Eq. (1) that there occurs the downward force because the projected area $S_9$ in the direction of movement of the moving plate 9 is larger than the sectional area $S_6$ of the piston.

$$Fd = Pa \cdot S_9 - Pa \cdot S_6 = Pa(S_9 - S_6) \quad (1)$$

Generally, when the apparatus of the present embodiment is used in medical treatment or surgery, an aspirating catheter (not illustrated) is connected to the forward end of the fluid guide tube 21 and is inserted into a treated area of a patient. The aspirating catheter may be dispensed with where a using condition permits.

To aspirate the fluid, the fluid inlet 4 is opened, thus a negative pressure is built up in the suction chamber 3, into which the liquid 2 is aspirated and collected from a wound or other part of the patient as shown in FIG. 1. Here, provided that the absolute pressure in the suction chamber 3 is Pb, the relative pressure to the atmospheric pressure (Pa–Pb) in the suction chamber 3 is derived as the following Eq. (3) from a formula (2) expressing the condition of equilibrium of forces acting on the piston 6 and the moving plate 9 which are connected as a unit. This calculation was done, neglecting the sectional area of the connecting rod 20 and the weight of the piston 6 and the moving plate 9. It is understood from Eq. (3) that in the suction chamber 3 there takes place a fixed negative pressure to be determined by the sectional area $S_6$ of the piston 6, the projected area $S_9$ in the direction of movement of the moving plate 9, and the atmospheric pressure Pa; the negative pressure being constant at all times without being changed by the amount of the fluid 2 aspirated.

$$Pa \cdot S_6 + (-Pa \cdot S_9) + Pb \cdot S_9 = 0 \quad (2)$$

$$Pb - Pa = -S_6 \cdot Pa / S_9 \quad (3)$$

The fluid 2 collected into the suction chamber 3 is discharged by disengaging the locking projection 18 of the cylinder 8 from the upper wall 12 of the case 14 after closing the fluid inlet 4, and then by pushing down the cylinder 8 with the fluid outlet 5 opened. In the prior art fluid aspiration-collection apparatus disclosed in Examined Japanese Patent Publication No. Sho 63-1859, it is likely that the outside air is let into the suction chamber with the discharge of the fluid, and viruses, various germs, etc. in the atmosphere enter the suction chamber, infecting the patient via the suction chamber. According to the present embodiment, since the outside air is hardly let into the suction chamber 3, the apparatus has an excellent infection prevention effect. Furthermore, if a scale is installed on the side wall of the case 14, the quantity of the fluid 2 thus aspirated can easily and accurately be read by the scale. Also, the apparatus, being simple in construction, can be built compactly and easily, whereby the scaling of the apparatus can be prevented. The apparatus, therefore, is excellent in portability and enables cost reduction. For example, in the fluid aspiration-collection apparatus disclosed in Examined Japanese Patent Publication No. Sho 63-1859, the negative pressure generating section and the fluid collecting section are separately provided. However, according to the present embodiment, as the aspiration section and the fluid collecting section are constituted in one suction chamber 3, it is possible to build the apparatus smaller in size than the prior art fluid aspiration-collection apparatus.

Second Embodiment

Figure 5:
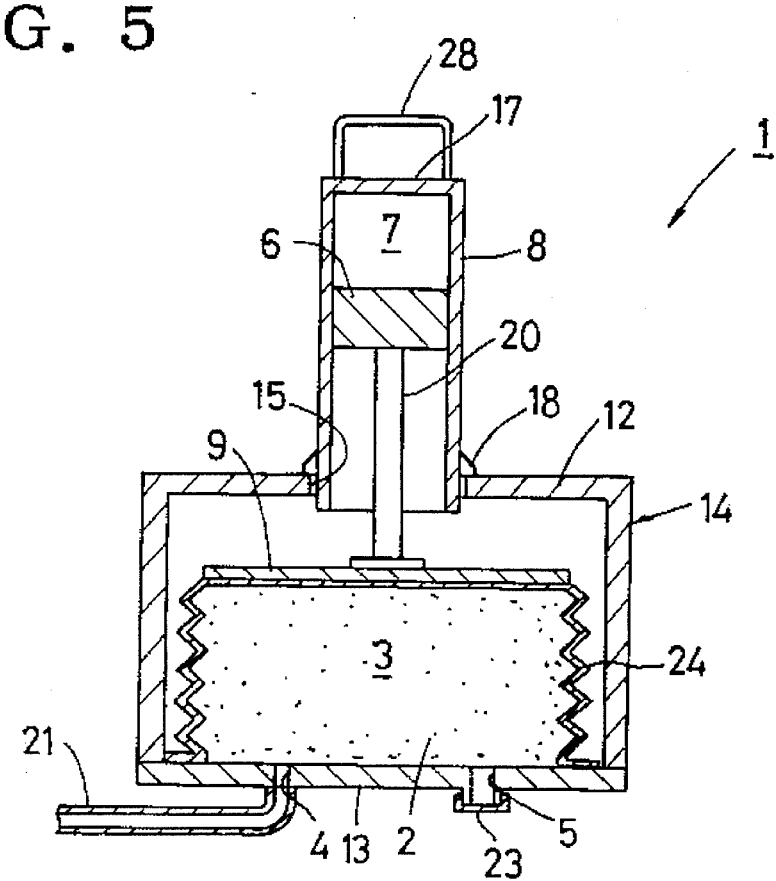
FIG. 5 is a sectional view of a second embodiment of the fluid aspiration-collection apparatus according to the present invention.

A second embodiment is shown in FIG. 5, wherein the same members as those in the first embodiment are designated by the same reference numerals and will not be explained.

In the fluid aspiration-collection apparatus of the present embodiment, the moving plate 9 does not slide in contact with the inside surface of the side wall of the case 14, and there is provided a cylindrical side wall portion 24 which constitutes the cylindrical member connecting the peripheral portion of the moving plate 9 with the lower wall 13 of the case 14. A space defined in this side wall portion 24 is the suction chamber 3. The side wall portion 24 is of a vertically expansible bellows-like structure, and therefore can increase and decrease the volume of the suction chamber 3 by moving the moving plate 9 vertically. Both the fluid inlet 4 and the fluid outlet 5 are provided in the lower wall 13 of the case 14, communicate with the suction chamber 3. The piston 6 is formed of an elastic member, such as silicone rubber, which is inserted slidably but airtightly in the cylinder.

Third Embodiment

Figure 6:
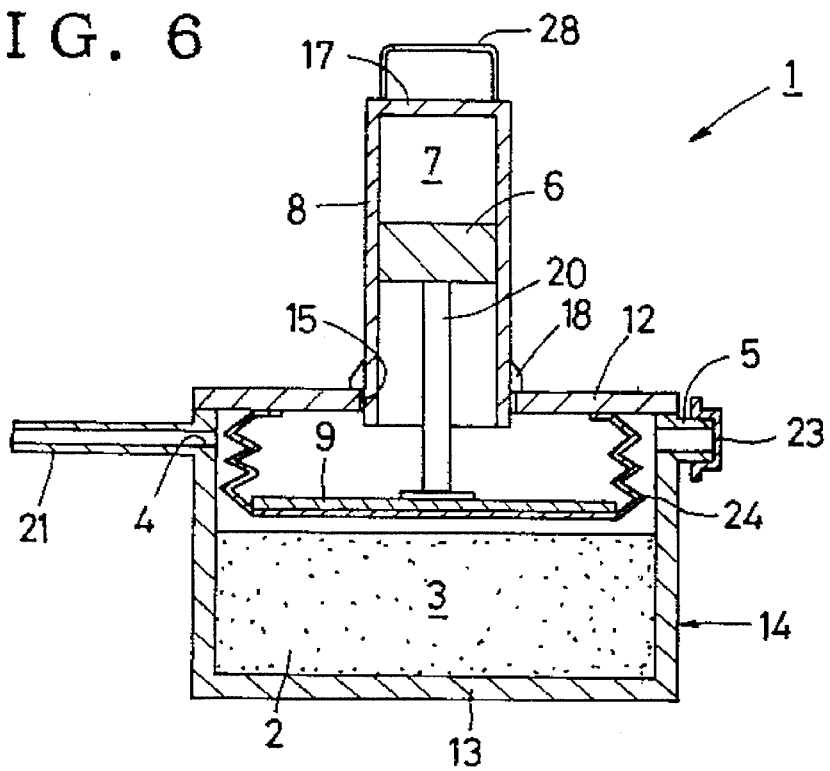
FIG. 6 is a sectional view of a third embodiment of the fluid aspiration-collection apparatus according to the present invention.

In a third embodiment shown in FIG. 6, a difference from the second embodiment described above lies in the point that the cylindrical side wall 24 is connected to the peripheral portion of the moving plate 9 and the upper wall 12 of the case 14. The apparatus is similar in other points of constitution and therefore like members are marked alike and will not be explained.

In the present embodiment, the suction chamber 3 is defined by the inner surface of the case, the outer peripheral surface of the side wall 24 and the lower surface of the moving plate 9. The quantity of fluid collected in the suction chamber 3 can be measured accurately by a scale provided on the side wall of the case 14.

Fourth Embodiment

Figure 7:
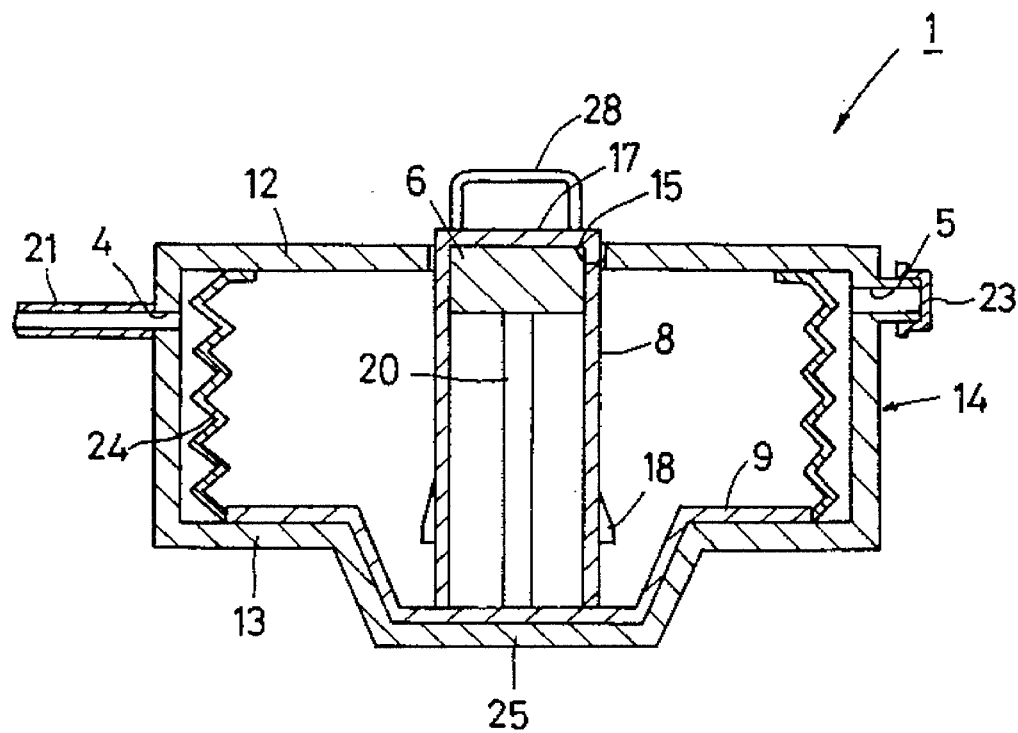
FIG. 7 is a sectional view of a fourth embodiment of the fluid aspiration-collection apparatus according to the present invention.

In a fourth embodiment shown in FIG. 7, a difference from the third embodiment described hereinabove resides in that the case 14 is provided with a downwardly protruding recess 25 at the center of the lower wall 13, and that the moving plate 9 is bent so as to fit in the recess 25. According to the present embodiment, it is possible to accurately measure the aspirated quantity of the fluid 2 during the initial period of aspiration, and to substantially secure the maximum amount of fluid that can be aspirated. In medical treatment, it is important to know the quantity of fluid aspirated from a wounded part immediately after operation, and the recess 25 of the fluid aspiration-collection apparatus 1 of the present embodiment is useful. Other points, being similar to the third embodiment, are marked by the same reference numerals and will not be explained.

Fifth Embodiment

Figure 8:
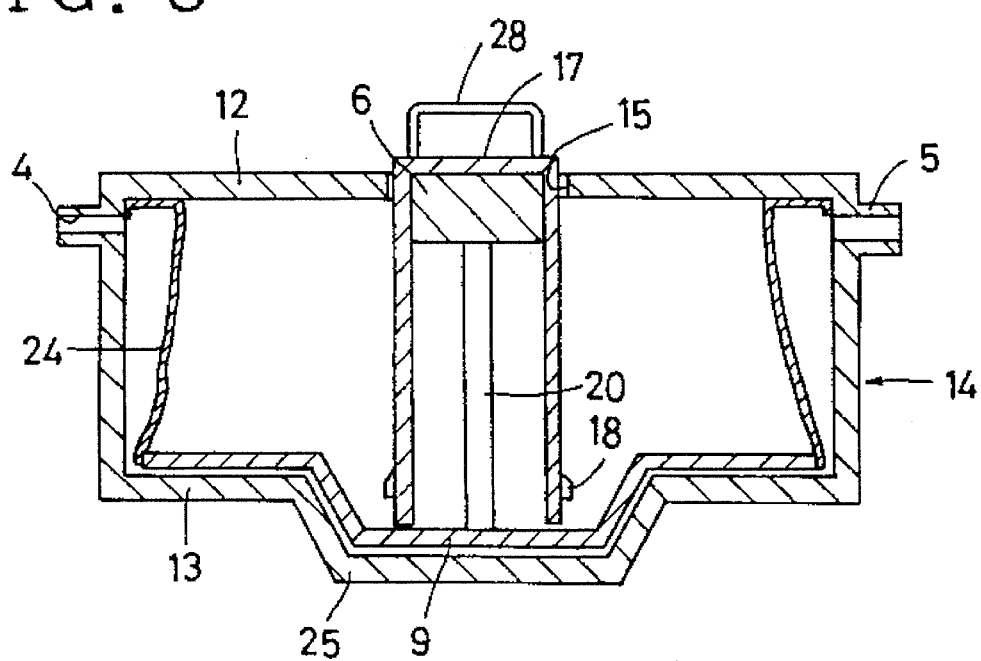
FIG. 8 is a sectional view of a fifth embodiment of the fluid aspiration-collection apparatus according to the present invention.

In a fifth embodiment shown in FIG. 8, a difference from the fourth embodiment described above lies in that the cylindrical side wall 24 of a flexible bag type has been adopted in place of the side wall 24 of the bellows construction; other points of the constitution, being the same as the fourth embodiment, are designated by the same reference numerals and will not be explained in detail.

Sixth Embodiment

Figure 9:
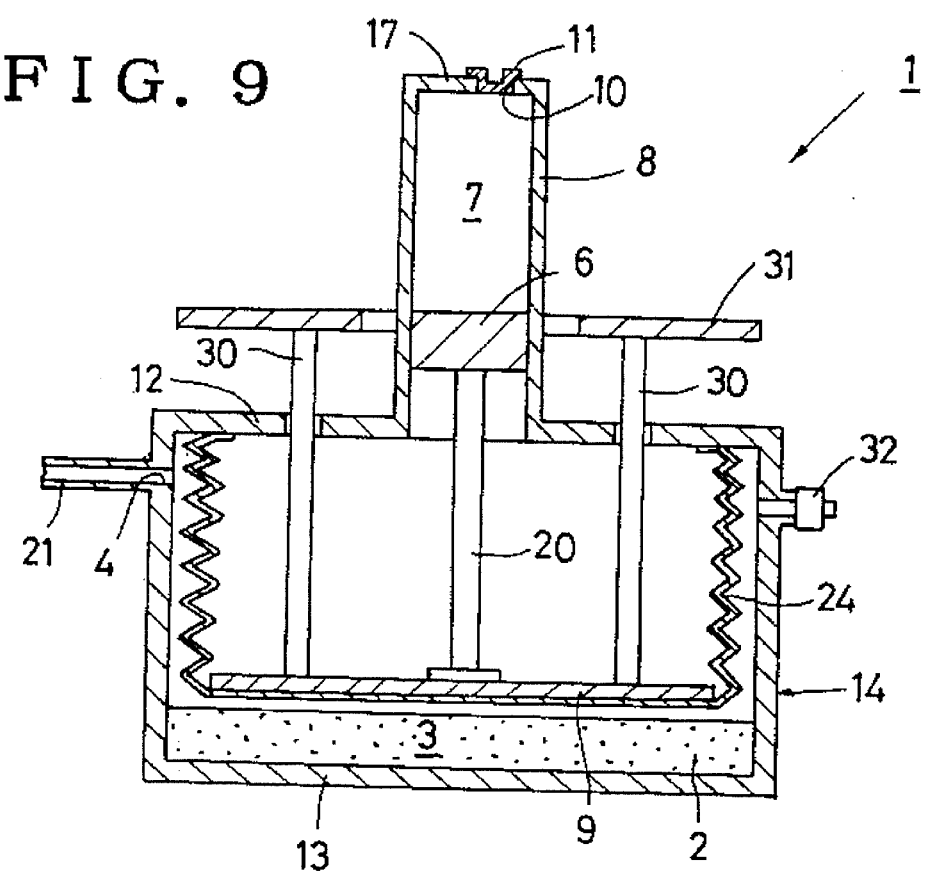
FIG. 9 is a sectional view of a sixth embodiment of the fluid aspiration-collection apparatus according to the present invention.
Figure 10:
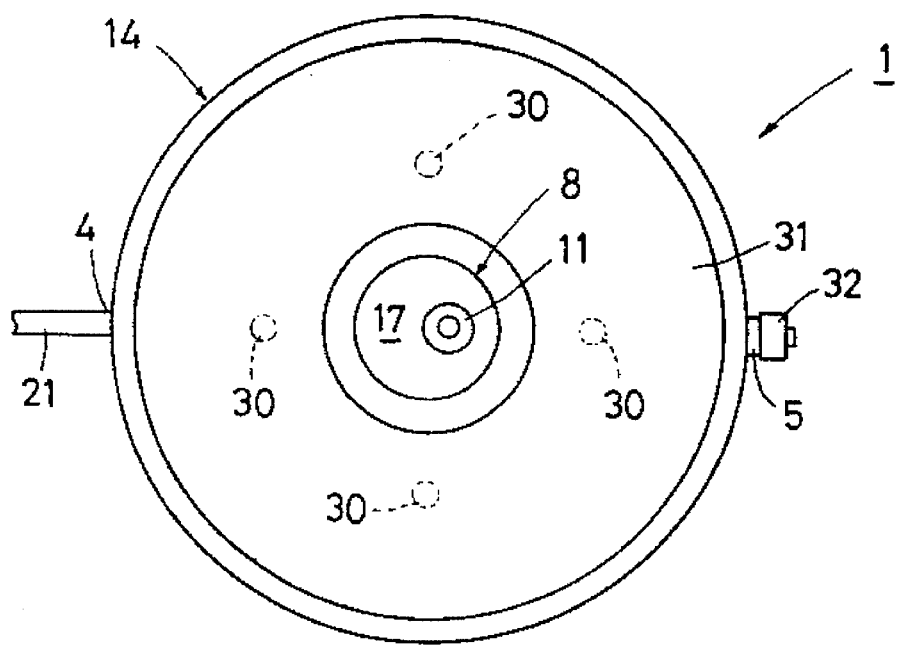
FIG. 10 is a plan view of FIG. 9.

In a sixth embodiment shown in FIGS. 9 and 10, the same members as those in the third embodiment described hereinabove are designated by the same reference numerals and will not be explained in detail. An explanation will be given only to different constitution and effect of operation.

In the present embodiment, the cylinder 8 is integrally secured to the upper wall 12 of the case 14, and an opening-closing means 11, such as a plug, which is capable of closing a communicating port 10 communicating with both the vacuum chamber 7 and the atmosphere is removably installed in the upper wall 17 of the cylinder 8. From the moving plate 9 four operating rods 30 extend upwardly, vertically movable through the upper wall 12 of the case 14. The top ends of these operating rods 30 are fixedly attached to an operating plate 31. At the fluid outlet 5 is installed a one-way valve 32 which allows the flow of a fluid or a gas from the inside of the suction chamber 3 only to the outside.

When the fluid aspiration-collection apparatus of the present embodiment is used, the operating plate 31 is positioned at the top end of stroke, that is, the piston 6 is held in contact with the upper wall 12 of the cylinder 8, with the communicating port 10 opened; from this state, the communicating port 10 is closed by the opening-closing means 11. Also, when the operating plate 31 is pushed downwardly with the fluid inlet 4 in a closed position, the air in the suction chamber 3 is discharged out at the one-way valve 32 mounted at the fluid outlet 5 and at the same time the vacuum chamber 7 is formed within the cylinder 8 owing to the relative movement of the piston 6 and the cylinder 8, thereby allowing the aspiration of the fluid 2 at a constant pressure by opening the fluid inlet 4.

To discharge the fluid 2 thus collected, the fluid inlet 4 is closed first, and then the operating plate 31 is pushed down. At this time the moving plate 9 moves downwardly, decreasing the volume of the suction chamber 3 to thereby drive the fluid 2 out at the one-way valve 32. At the same time the vacuum chamber 7 is formed and the fluid inlet 4 is opened to permit re-aspiration. The downward movement of the moving plate 9, as a matter of course, can be done with ease by opening the communicating port 10 to the atmosphere when discharging the fluid 2.

Seventh embodiment

Figure 11:
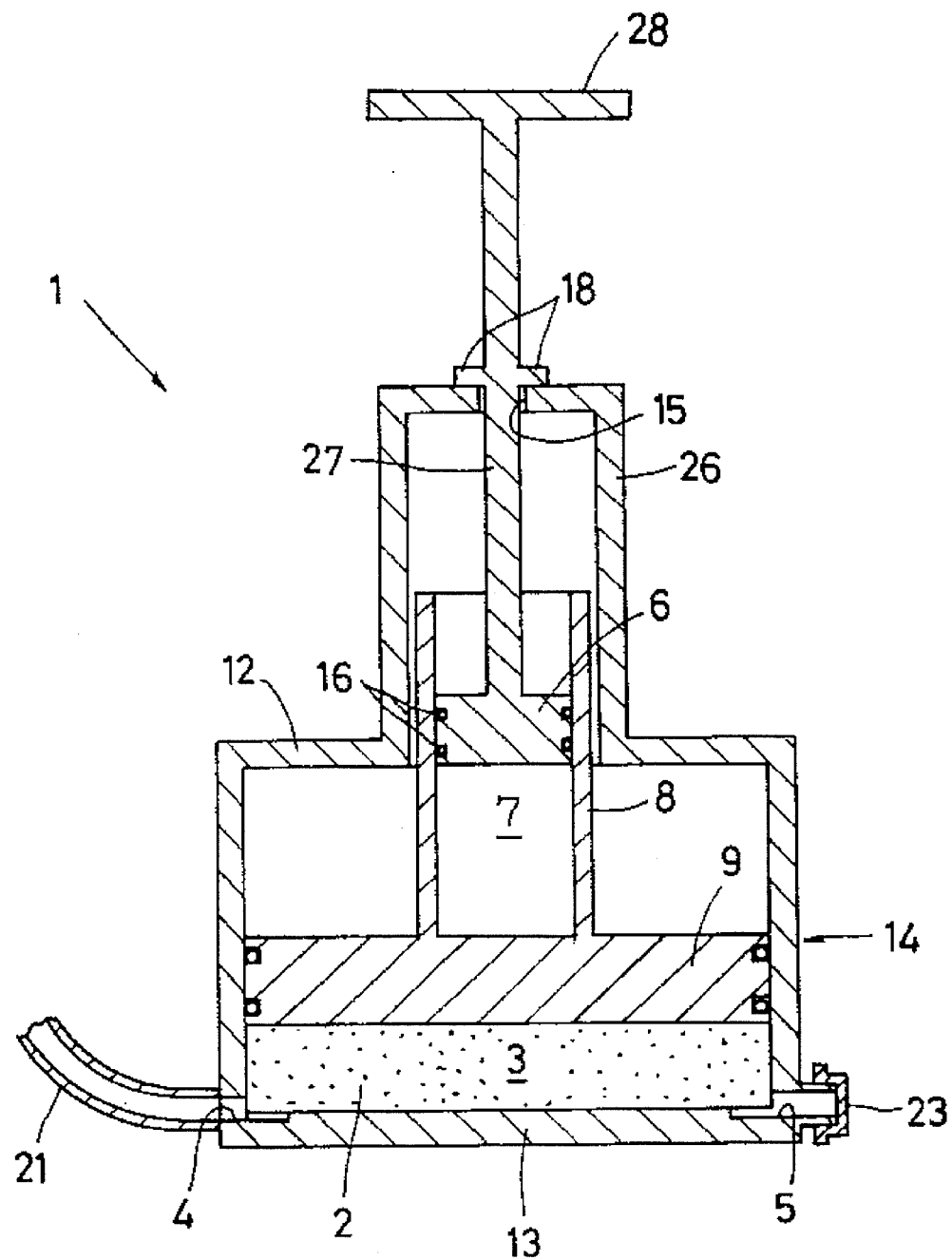
FIG. 11 is a sectional view of a seventh embodiment of the fluid aspiration-collection apparatus according to the present invention.

In a seventh embodiment shown in FIG. 11, the same members as those in the first embodiment described hereinabove are designated by the same reference numerals and will not be explained. An explanation will be given only to different constitution.

In the present embodiment, the cylinder 8 which opens in the top is provided as a unit on the back side of the moving plate 9 and a cylindrical cylinder guide section 26 is molded as a unit on the upper part of the case 14. On the top of the piston 6 vertically slidably inserted in the cylinder 8 is extendedly provided an operating rod 27, which protrudes upwards through the round hole 15 provided in the upper wall 12 of the cylinder guide section 26. On the top end of the operating rod 27 is provided a handle 28 as one unit.

Next, a method of manufacturing the fluid aspiration-collection apparatus of the present embodiment will be briefly explained. Prior to assembling each member, the handle 28 is not secured to the operating rod 27; that is, the handle 28 is prepared as a separate member, and the lower wall 13 of the case 14 is also not fixedly installed to the casing body. To assemble each member, first the cylinder 8 is molded integrally with the back side of the moving plate 9 and is installed so that the piston 6 molded integrally with the operating rod 27 will be in contact with the bottom surface of the cylinder 8. In the moving plate 9 is formed an exhaust port (not illustrated) communicating with the interior of the cylinder 8. After the insertion of the piston 6, the exhaust port will be closed. After the installation, in the casing body, of the moving plate 9 and the cylinder 8 into which the piston 6 has been inserted, the lower wall 13 is secured by welding or the like. At this time the operating rod 27 protrudes out of the round hole 15. On the top end of the operating rod 27 which extrudes, the handle 28 is fixedly attached by welding or the like.

According to the present embodiment, when the operating rod 27 is pulled up with the fluid inlet 4 and the fluid outlet 5 is closed, the vacuum chamber 7 is created within the cylinder 8. When the locking projection 18 projectingly provided on the operating rod 27 has appeared above the upper surface of the cylinder guide section 26, the operating rod 27 is rotated to lock the locking projection 18 on the upper surface of the cylinder guide section 26, thereby holding the operating rod 27 and accordingly the piston 6 in a specific position. The following operation is the same as that of the first embodiment.

Eighth Embodiment

Figure 12:
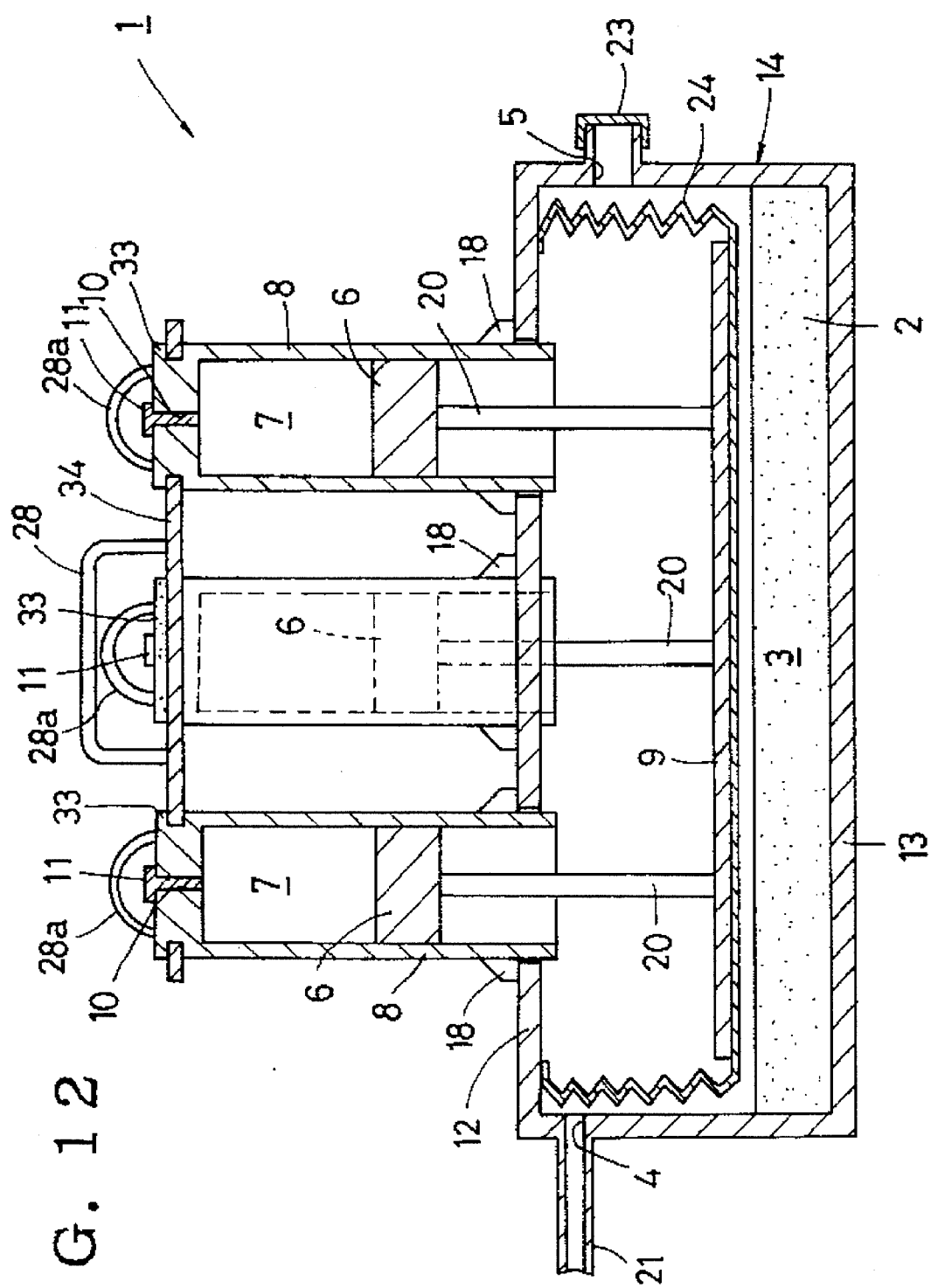
FIG. 12 is a sectional view of an eighth embodiment of the fluid aspiration-collection apparatus according to the present invention.
Figure 13:
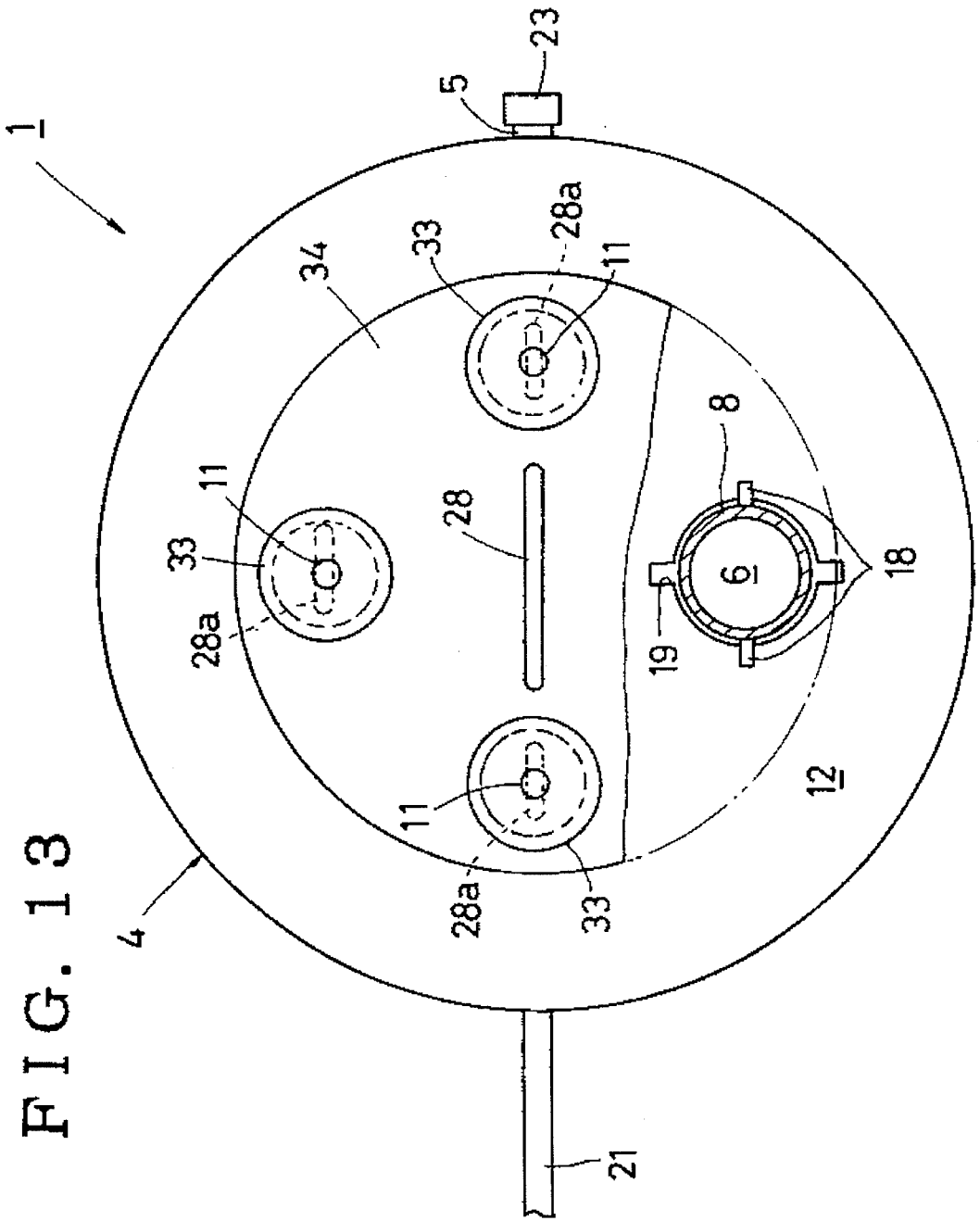
FIG. 13 is a plan view of FIG. 12.

In an eighth embodiment shown in FIGS. 12 and 13, the same members as those in the third embodiment described hereinabove are designated by the same reference numerals and will not be explained. An explanation will be given only to different constitution and effect of operation.

In the present embodiment, the apparatus has four sets of pistons 6 and cylinders 8. Each of the pistons 6 is integrally connected with the moving plate 9 and each of the cylinders 8 is inserted in the round hole 15 provided in the upper wall 12 of the case 14. At the upper part of each cylinder 8 is formed a flange section 33, which is rotatably mounted on the connecting plate 34. The four cylinders 8 can be pulled upwardly all together by pulling the handle 28 of the connecting plate 34 upwardly. At this time, the locking projection 18 passes through the cutout 19 provided in the inner periphery of the round hole 15 of the upper wall 12. Then, each cylinder 8 is rotated to move the locking projection 18 into engagement with the upper wall 12 of the case 14. At the center of the upper wall 17 of each cylinder 8 is provided a communicating hole 10 which is open to the atmosphere; in this communicating hole 10 the plug-like opening-closing means 11 is fitted airtightly.

Figure 14:
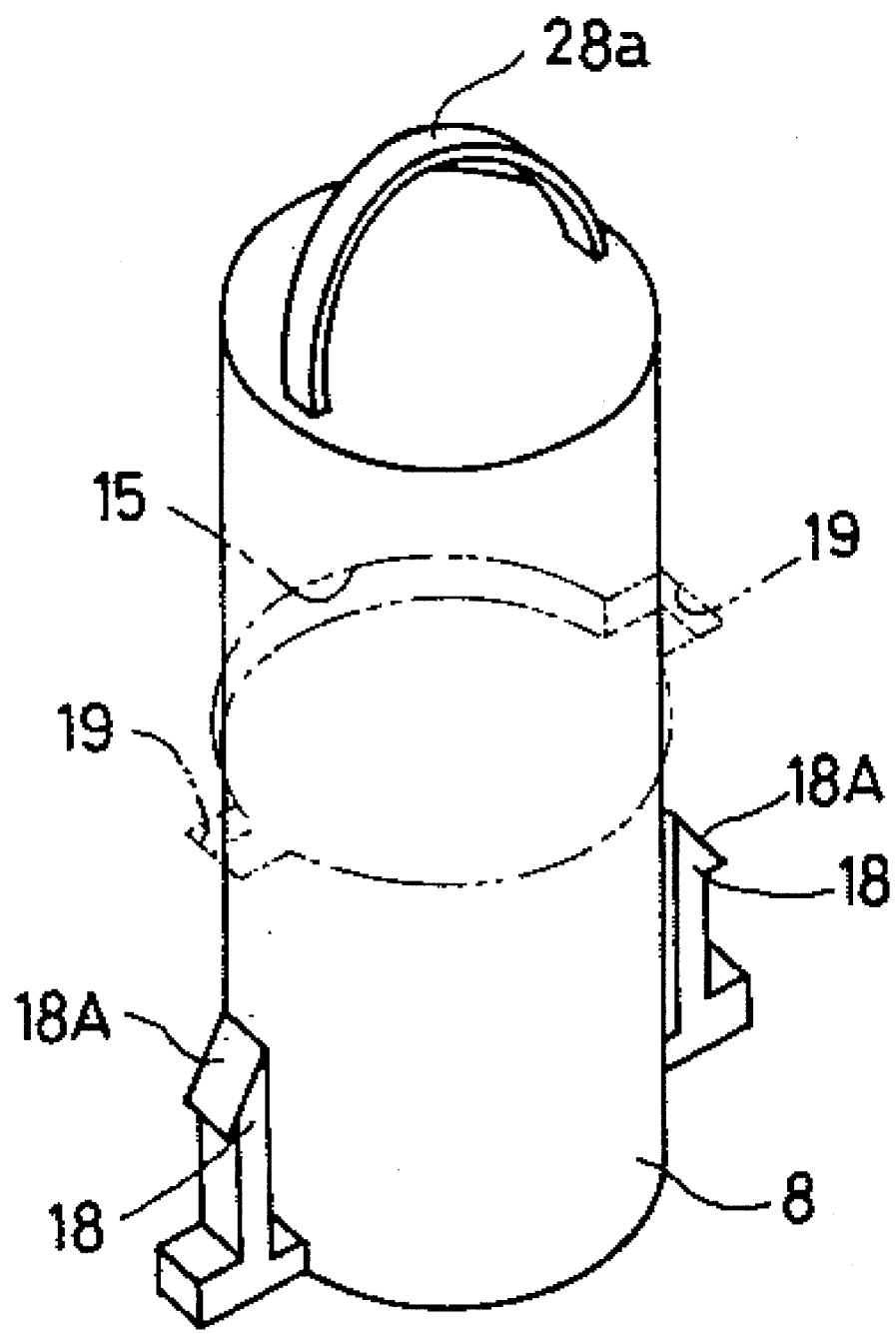
FIG. 14 is a perspective view of a cylinder showing a modification of locking projections.

It is advisable that the locking projection 18, as shown in FIG. 14, be so constituted as to be elastically movable in a radial direction, and be provided, at the top end, with a taper surface 18A which contacts the inner surface of the cutout 19 to deform the locking projection 18 radially inwardly. In the apparatus of the above-described constitution, the locking projections 18 of the four cylinders 8 can be engaged with the cutouts 19 of the case 14 merely by pulling up the handle 28 of the connecting plate 34. To disengage, the locking projections 18 is simply pushed radially inwardly. The constitution of the locking projection 18 shown in FIG. 14 can be adopted also in each of the embodiments described hereinabove. The communicating port 10 and the opening-closing means 11 are not required to be provided in all of the cylinders 8, but are sufficient if provided in at least one of the cylinders 8.

According to the present embodiment, suction pressure adjustment on the whole can be done by opening and closing the communicating port 10 by the opening-closing means 11 pursuant to necessity. In the present embodiment, the cylinders 8 are connected each to the connecting plate 34, but may be so constituted as to be pulled up separately without the provision of the connecting plate 34. In this case, aspiration is done with the fluid inlet 4 opened after forming the vacuum chamber 7 by pulling up as many cylinders 8 as required.

It should be noted that each embodiment of the present invention explained hereinabove is not limited thereto and design changes are possible within the scope of the present invention. For example, the piston 6 and the moving plate 9 in the described embodiments are connected With each other by the connecting rod 20, but may be connected by a wire-like material such as a string, wire, and so forth. It also should be noticed that the fluid aspiration-collection apparatus of the present invention is not limited to the embodiments for medical use explained above and is usable for various other purposes.

What is claimed is:

1. A fluid aspiration-collection apparatus comprising:

a case having a liquid inlet and a liquid outlet and provided with a hole in a top wall thereof;

a moving plate vertically movably disposed within the case so as to form a liquid suction chamber between the moving plate and a bottom wall of the case;

a cylinder having an upper end provided with an upper wall and an open lower end, the cylinder being vertically movably inserted into the hole from above the top wall of the case in such a manner that the opened lower end thereof is positioned in the case;

a piston airtightly and movably inserted in the cylinder and having a sectional area smaller than a projected area of the moving plate in the moving direction thereof;

a connecting rod vertically extending to connect the piston cooperatively to the moving plate;

holding means for maintaining the cylinder at a lifted position to which the cylinder is forcibly drawn upward to form a vacuum chamber between the piston and the top surface of the cylinder: and closable means for communicating said cylinder with the atmosphere.

2. A fluid aspiration-collection apparatus as set forth in claim 1, wherein said closable means comprises said upper wall of said cylinder defining a communicating port through which the inside of said cylinder communicates with the atmosphere and which is closable and openable by an opening-closing member removably provided to the communicating port.

3. A fluid aspiration-collection apparatus as set forth in claim 2, wherein said hole of said top wall comprises a plurality of holes, said cylinder comprises a plurality of cylinders each inserted through each of the plurality of holes, and said piston comprises a plurality of pistons each inserted in each of the cylinders and cooperatively connected to said moving plate.

4. A fluid aspiration-collection apparatus as set forth in claim 3, further comprising a vertically expansible cylindrical member having an upper end airtightly attached to an inner surface of said top wall and a lower end airtightly attached to an upper surface of said moving plate, wherein said suction chamber comprises an internal space of the case existing outside and below the cylindrical member.

5. A fluid aspiration-collection apparatus as set forth in claim 4, wherein the outer periphery of said cylindrical member is of a bellow structure.

6. A fluid aspiration-collection apparatus as set forth in claim 5, wherein said holding means includes a locking projection radially outwardly projecting from a lower peripheral surface of said cylinder so as to be capable of hooking the peripheral edge of said hole of said top wall, and a notch portion formed at the peripheral edge of said hole to permit the locking projection to pass therethrough.

7. A fluid aspiration-collection apparatus as set forth in claim 5, wherein said holding means includes a locking projection which is elastically deformable radially of said cylinder and is projecting radially outwardly from a lower peripheral surface of said cylinder so as to be capable of hooking the peripheral edge of said hole of said top wall, the locking projection having a tapered surface at the upper end thereof which is adapted to radially deform the locking projection when brought into contact with the peripheral edge of said hole of the top wall.

8. A fluid aspiration-collection apparatus as set forth in claim 2, wherein said moving plate is disposed liquid-tightly and movably with respect to the inner periphery of said case, and said suction chamber comprises a space defined by the underside of said moving plate and an inner peripheral surface of said casing.

9. A fluid aspiration-collection apparatus as set forth in claim 8, wherein said holding means includes a locking projection radially outwardly projecting from a lower peripheral surface of said cylinder so as to be capable of hooking the peripheral edge of said hole of said top wall, and a notch portion formed at the peripheral edge of said hole to permit the locking projection to pass therethrough.

10. A fluid aspiration-collection apparatus as set forth in claim 8, wherein said holding means includes a locking projection which is elastically deformable radially of said cylinder and is projecting radially outwardly projecting from a lower peripheral surface of said cylinder so as to be capable of hooking the peripheral edge of said hole of said top wall, the locking projection having a tapered surface at the upper end thereof which is adapted to radially deform the locking projection when brought into contact with the peripheral edge of said hole of the top wall.

11. A fluid aspiration-collection apparatus as set forth in claim 2, further comprising a vertically expansible cylindrical member having an upper end liquid-tightly attached to the underside of said moving plate and a lower end liquid-tightly attached to an inner surface of said bottom wall of said case, wherein said suction chamber comprises an internal space of the cylindrical member.

12. A fluid aspiration-collection apparatus as set forth in claim 11, wherein the outer periphery of said cylindrical member is of a bellow structure.

13. A fluid aspiration-collection apparatus as set forth in claim 12, wherein said holding means includes a locking projection radially outwardly projecting from a lower peripheral surface of said cylinder so as to be capable of hooking the peripheral edge of said hole of said top wall, and a notch portion formed at the peripheral edge of said hole to permit the locking projection to pass therethrough.

14. A fluid aspiration-collection apparatus as set forth in claim 12, wherein said holding means includes a locking projection which is elastically deformable radially of said cylinder and is projecting radially outwardly from a lower peripheral surface of said cylinder so as to be capable of hooking the peripheral edge of said hole of said top wall, the locking projection having a tapered surface at the upper end thereof which is adapted to radially deform the locking projection when brought into contact with the peripheral edge of said hole of the top wall.

15. A fluid aspiration-collection apparatus as set forth in claim 2, further comprising a vertically expansible cylindrical member having an upper end airtightly attached to an inner surface of said top wall and a lower end airtightly attached to an upper surface of said moving plate, wherein said suction chamber comprises an internal space of the case existing outside and below the cylindrical member.

16. A fluid aspiration-collection apparatus as set forth in claim 15, wherein said bottom wall of said case has a downwardly protruding recess in a central portion thereof, said moving plate has a downwardly protruding recess in a central portion thereof which is adapted to be fitted into the recess of said bottom wall and to receive a lower portion of said cylinder in a lowered position.

17. A fluid aspiration-collection apparatus as set forth in claim 16, wherein the outer periphery of said cylindrical member is of a bellow structure.

18. A fluid aspiration-collection apparatus as set forth in claim 17, wherein said holding means includes a locking projection radially outwardly projecting from a lower peripheral surface of said cylinder so as to be capable of hooking the peripheral edge of said hole of said top wall, and a notch portion formed at the peripheral edge of said hole to permit the locking projection to pass therethrough.

19. A fluid aspiration-collection apparatus as set forth in claim 18, wherein said holding means includes a locking projection which is elastically deformable radially of said cylinder and is projecting radially outwardly from a lower peripheral surface of said cylinder so as to be capable of hooking the peripheral edge of said hole of said top wall, the locking projection having a tapered surface at the upper end thereof which is adapted to radially deform the locking projection when brought into contact with the peripheral edge of said hole of the top wall.

* * * * *